(12) United States Patent
Rozen et al.

(10) Patent No.: US 9,606,064 B2
(45) Date of Patent: Mar. 28, 2017

(54) METHOD OF DETECTING IRREGULAR CURRENT FLOW IN AN INTEGRATED CIRCUIT DEVICE AND APPARATUS THEREFOR

(75) Inventors: Anton Rozen, Gedera (IL); Leonid Fleshel, Hertzelia (IL); Michael Priel, Netanya (IL); Yoav Weizman, Kfar-Vitkin (IL)

(73) Assignee: NXP USA, INC., Austin, TX (US)

( * ) Notice: Subject to any disclaimer, the term of this patent is extended or adjusted under 35 U.S.C. 154(b) by 233 days.

(21) Appl. No.: 14/380,738

(22) PCT Filed: Feb. 27, 2012

(86) PCT No.: PCT/IB2012/050899
§ 371 (c)(1),
(2), (4) Date: Aug. 25, 2014

(87) PCT Pub. No.: WO2013/128234
PCT Pub. Date: Sep. 6, 2013

(65) Prior Publication Data
US 2015/0015240 A1    Jan. 15, 2015

(51) Int. Cl.
*G01N 21/66* (2006.01)
*G01R 15/24* (2006.01)
*G01R 31/311* (2006.01)

(52) U.S. Cl.
CPC ............ *G01N 21/66* (2013.01); *G01R 15/24* (2013.01); *G01R 31/311* (2013.01)

(58) Field of Classification Search
CPC .. G01R 31/311; G01R 31/308; G01R 31/302; G01R 31/3008; G01R 31/309; G01R 31/265; G01R 31/2656; G01R 31/2884; G01R 15/24; G06F 11/24; G01N 21/62; G01N 21/66
See application file for complete search history.

(56) References Cited

U.S. PATENT DOCUMENTS

| 4,584,523 A | 4/1986 | Elabd |
| 6,049,218 A * | 4/2000 | Storino .................. G01R 31/30 324/750.3 |

(Continued)

OTHER PUBLICATIONS

International Search Report and Written Opinion correlating to PCT/IB2012/050899 dated Nov. 14, 2012.

(Continued)

*Primary Examiner* — Huy Q Phan
*Assistant Examiner* — David Frederiksen (57) ABSTRACT

A method of detecting irregular high current flow within an integrated circuit (IC) device is described. The method comprises obtaining infrared (IR) emission information for the IC device, identifying at least one functional component within the IC device comprising a high current flow, based at least partly on the obtained IR emission information, obtaining IR emission information for at least one reference component within the IC device, and determining whether the high current flow of the at least one functional component comprises an irregular high current flow based at least partly on a comparison of respective IR emission information for the at least one functional component and the at least one reference component.

15 Claims, 2 Drawing Sheets

(56) References Cited

U.S. PATENT DOCUMENTS

| | | | | |
|---|---|---|---|---|
| 6,066,956 | A | * | 5/2000 | Nikawa ............... G01R 31/311 |
| | | | | 324/754.23 |
| 7,151,387 | B2 | | 12/2006 | Weizman et al. |
| 7,248,059 | B1 | | 7/2007 | Ochoco |
| 7,323,862 | B2 | | 1/2008 | Desplats et al. |
| 7,426,448 | B2 | | 9/2008 | Song et al. |
| 8,278,959 | B2 | * | 10/2012 | Chua ................... G01R 31/311 |
| | | | | 324/754.21 |
| 2003/0137318 | A1 | * | 7/2003 | Enachescu ........... G01R 31/308 |
| | | | | 324/760.01 |
| 2004/0027083 | A1 | | 2/2004 | Suzuki |
| 2004/0130914 | A1 | | 7/2004 | Abe |
| 2008/0238435 | A1 | * | 10/2008 | Bockelman .......... G01R 31/311 |
| | | | | 324/501 |
| 2009/0003685 | A1 | * | 1/2009 | Nikawa ............... G01R 31/311 |
| | | | | 382/149 |
| 2009/0119042 | A1 | * | 5/2009 | Meng ..................... G06F 11/24 |
| | | | | 702/66 |
| 2012/0201527 | A1 | * | 8/2012 | Lo ......................... H04N 5/238 |
| | | | | 396/213 |

OTHER PUBLICATIONS

Toriumi, Akira et al: "A Study of Photon Emission from n-Channel MOSFET's" IEEE Transactions on Electron Devices, vol. ED-34, No. 7, Jul. 1987, pp. 1501-1508.

\* cited by examiner

METHOD OF DETECTING IRREGULAR CURRENT FLOW IN AN INTEGRATED CIRCUIT DEVICE AND APPARATUS THEREFOR

FIELD OF THE INVENTION

This invention relates to a method and apparatus for detecting irregular current flow in an integrated circuit (IC) device.

BACKGROUND OF THE INVENTION

Infrared (IR) emission technique is an efficient technique for debugging very large scale integration (VLSI) integrated circuit (IC) devices, wherein IR emissions from an IC device during operation indicate drainage currents within the device. In this manner, IR emissions may be used to detect points with unexpected current consumption, and in particular points with unexpectedly high current consumption, thereby enabling localisation of a problematic design within the IC device. Estimation of a drainage current value is critical for distinguishing between a normal functional device and a problematic one; the current value being proportional to the 'brightness' (i.e. the amount of IR radiation emitted and other spectral characteristics) of the respective IR 'hotspot'. For example, during normal operation an IC component may be biased to consume a constant level of current, such as may occur within a current mirror, voltage divider, etc. Additionally and/or alternatively, a leakage related emission may occur during normal operation, for example from 'turned off' transistor components. As such, it is important to be able to differentiate between such currents occurring during normal operation and drainage currents occurring from faulty behaviour.

However, the brightness of IR hotspots has not scaled proportionally with the scaling of modern IC devices. As such, although IR emission technique is still an effective technique for identifying high current flow within modern IC devices, the calibration of test equipment to determine current values based on the brightness of IR hotspots is becoming increasingly more difficult with the lower current values of modern IC devices. For example, typical leakage currents may be in the order of nA to several µA, depending on the bias conditions and expected behaviour. Identifying points with unexpected/irregular current consumption is particularly problematic when there are numerous IR emission hotspots located close to one another, since it is almost impossible to make an accurate current summation for each of the individual drainage sources therefor.

SUMMARY OF THE INVENTION

The present invention provides a method of detecting irregular high current flow within an integrated circuit (IC) device, an apparatus comprising at least one signal processing module arranged to perform the method of detecting irregular high current flow within an IC device, non-transitory computer program product having computer-readable code stored thereon for programming a signal processing module to perform a method of detecting irregular high current flow within an IC device, and an IC device as described in the accompanying claims.

Specific embodiments of the invention are set forth in the dependent claims.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
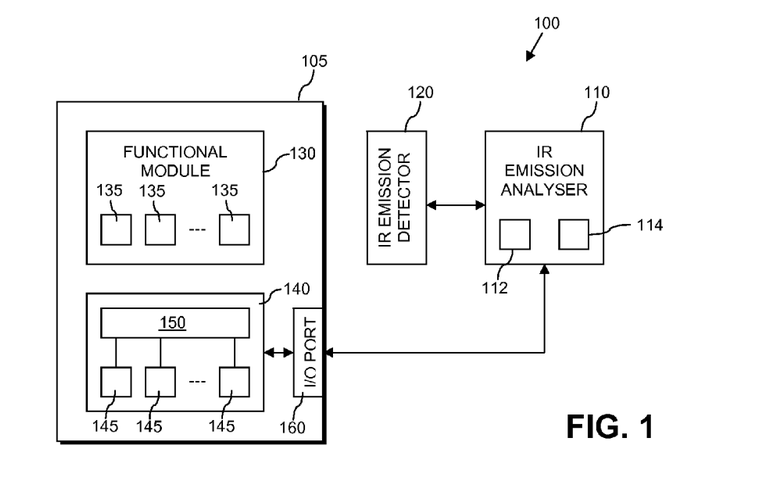
FIG. 1 illustrates a simplified block diagram of an example of an apparatus arranged to perform infrared emission analysis of integrated circuit (IC) devices.

Referring first to FIG. 1, there is illustrated a simplified block diagram of an example of an apparatus 100 arranged to perform infrared emission analysis of integrated circuit (IC) devices, such as the IC device illustrated at 105. Because the illustrated embodiments of the present invention may for the most part, be implemented using electronic components and circuits known to those skilled in the art, details will not be explained in any greater extent than that considered necessary as illustrated below, for the understanding and appreciation of the underlying concepts of the present invention and in order not to obfuscate or distract from the teachings of the present invention.

In the example illustrated in FIG. 1, the apparatus 100 comprises an IR emission analyser 110. The IR emission analyser 110 comprises one or more signal processing modules, such as illustrated generally at 112, arranged to perform a method of detecting irregular high current flow within an IC device. For example, the signal processing module(s) may be arranged to execute computer-readable code stored within one or more non-transitory computer program products, such as illustrated generally at 114, such computer-readable code being operable for performing the method of detecting irregular high current flow within an IC device.

As used herein, the expression non-transitory will be understood to refer to the non-ephemeral nature of the storage medium itself rather than to a notion of how long the stored information itself may persist in a stored state. Accordingly, memories that might otherwise be viewed, for example, as being volatile (such as many electronically-erasable programmable read-only memories (EPROM's) or random-access memories (RAM's)) are nevertheless to be viewed here as being 'non-transitory' whereas a signal carrier in transit is to be considered 'transitory' notwithstanding that the signal may remain in transit for a lengthy period of time. Accordingly, it is contemplated that such non-transitory computer program products 114 may comprise, by way of example only, at least one of a hard disk, a CD-ROM, an optical storage device, a magnetic storage device, a Read Only Memory (ROM), a Programmable Read Only Memory (PROM), an Erasable Programmable Read Only Memory (EPROM), an Electrically Erasable Programmable Read Only Memory (EEPROM) and a Flash memory.

In accordance with some example embodiments, the signal processing module(s) 112 of the IR emission analyser 110 is arranged to obtain IR emission information for functional modules within the IC device 105. In the example illustrated in FIG. 1, the IC device 105 comprises one or more functional modules, illustrated generally at 130, arranged to perform one or more operational functions of the IC device 105. The, or each, functional module 130 may represent, say, a particular power domain within the IC device 105. The (or each) functional module 130 comprises functional components 135. IR emission information for the functional module(s) 130 may comprise, for example, information relating to an emitted IR signature and intensity therefor, and may be obtained in any suitable manner, for example by way of an IR emission detector 120 operably coupled to the IR emission analyser 110. Such IR emission detectors 120 are well known in the art, and as such the IR emission detector 120 will not be described in further detail herein. Nevertheless, for completeness, such an IR emission detector 120 may comprise any suitable device capable of capturing IR emission information, for example such as a camera capable of performing IR emission microscopy.

Having obtained the IR emission information for the functional module(s) 130 of the IC device 105, the signal processing module(s) 112 of the IR emission analyser 110 is/are then arranged to identify functional components 135 within the IC device 105 comprising high current flows, based at least partly on the obtained IR emission information. For example, a high current flow within the IC device 105 may be detected by way of, say, an IR emission intensity greater than a predetermined threshold, for example defined by threshold emission due to leakage emission or due to normally operated circuit. Accordingly, the signal processing module(s) 112 of the IR emission analyser 110 may be arranged to identify IR emissions within the IR emission information obtained for the functional module(s) 130 of the IC device 105 comprising an intensity greater than such a predetermined threshold; herein after referred to as 'high intensity' IR emissions. Subsequently, for each identified high intensity emission, a functional component 135 located at a position within the IC device 105 corresponding to the identified high intensity emission may then be identified as comprising a respective high current flow. For example, the IR emission information may comprise two-dimensional positioning information relating to the IR emission information, enabling the IR emission information to be related to a two-dimensional spatial reference. The signal processing module(s) 112 of the IR emission analyser 110 may also be provided with component position information for the functional module(s) 130 of the IC device 105, with the component position information for the IC device 105 being related to the same two-dimensional spatial reference as the IR emission information. In this manner, each identified high intensity emission may be associated with a point relative to the two-dimensional spatial reference. A functional component 135 of the IC device 105 positioned at a corresponding location within the IC device 105 relative to the two-dimensional spatial reference may then be identified as comprising the associated high current flow. In some examples, a 'high' drainage current may comprise a current value of more than, say, 20% higher than current flows indicative of correct, normal operation. Accordingly, in a case where a current value indicative of correct, normal operation is in the range of, say, 10 nA/um, the IR emission intensity threshold used, in the above example, to detect high current flows may be approximately calibrated such that drainage currents above, say 12 nA/um are detected.

The signal processing module(s) 112 of the IR emission analyser 110 is/are further arranged to obtain IR emission information for one or more reference component(s) within the IC device 105. For example, the IC device 105 in FIG. 1 further comprises at least one IR emission reference module 140 comprising at least one IR emission reference component 145. The (or each) IR emission reference component 145 is arranged to comprise IR emission spectral properties corresponding to those of at least one functional component 135; for example comprising a corresponding IR signature.

Accordingly, in the illustrated example the signal processing module(s) 112 of the IR emission analyser 110 may be arranged to obtain IR emission information for one or more of the IR emission reference components 145 within the IC device 105. Such IR emission information may be obtained by way of appropriate spectral analysis of the IR emissions therefore, for example as described in: "A Study of Photon Emission from n-Channel MOSFET's" TORIUMI et al, IEEE TRANSACTIONS ON ELECTRON DEVICES, VOL. ED-34, NO. 7, JULY 1987. In some examples, the IR emission information for the reference component(s) 145 may be obtained along with the IR emission information for the functional component(s) 135 of the IC device 105. Alternatively, the IR emission information for the reference component(s) 145 may subsequently be obtained, for example following configuration of one or more bias conditions for the reference component(s) 145 as described in greater detail below.

The signal processing module(s) 112 of the IR emission analyser 110 may then determine whether the (or each) high current flow of the functional component(s) comprises an irregular high current flow based at least partly on a comparison of the IR emission information for the respective functional component 135 with the IR emission information for the respective reference component 145. For example, the signal processing module(s) 112 may be arranged to perform a comparison of the IR emission information for the functional component(s) 135 and the IR emission information for the respective reference component(s) 145, and to determine that the (or each) high current flow of the respective functional component(s) 135 comprises an irregular high current flow if an IR emission intensity for the functional component 135 exceeds an IR emission intensity for the respective reference component 145. In some examples, in order to take into consideration slight variations in operating conditions etc. between the functional and reference components 135, 145, the signal processing module(s) 112 may be arranged to determine that the (or each) high current flow of the functional component(s) 135 comprises an irregular high current flow if an IR emission intensity for the functional component 135 exceeds an IR emission intensity for the respective reference component 145 by more than a threshold amount.

In this manner, differentiation between expected/intended high current flows indicative of correct, normal operation of the functional components 135, and unexpected/irregular high current flows indicative of incorrect, problematic operation of the functional component 135 within the IC device 105 may be achieved with significantly reduced calibration requirements for test equipment such as the IR emission analyser 110, significantly simplifying the process of identifying points with unexpected/irregular current consumption, in particular when there are numerous IR emission hotspots within the same power domain of an IC device. In particular, in the illustrated example the use of reference component 145 provides IR emission reference 'signatures' which can be used as references for IR 'hotspots' identified within the functional module(s) 130 of the IC device 105, enabling irregular current flows indicative of problematic operation to be detected.

In some examples, the IR emission reference module may comprise a plurality of IR emission reference components 145 comprising different IR emission spectral properties. Accordingly, the signal processing module(s) 112 of the IR emission analyser 110 may be arranged to identify, from the plurality of reference components 145, a reference component comprising IR emission spectral properties corresponding to, or closest to, those of a functional component identified as comprising a high current flow, obtain IR emission information for the identified reference component 145, and determine whether the high current flow of the respective functional component 135 comprises an irregular high current flow based at least partly on a comparison of respective IR emission information for the functional component 135 and the identified reference component 145.

In some examples, in order to obtain comparable IR emission information for the functional components 135 and the reference components 145, IR emission information may be obtained for reference component(s) 145 comprising at least one bias condition corresponding to one or more bias conditions of the respective functional component(s) 135 that have been identified as comprising the high current flow(s). For example, the IC device 105 illustrated in FIG. 1 comprises a plurality of IR emission reference components 145. In some examples, the IC device 105 may comprise a plurality of IR emission reference components 145 comprising IR emission spectral characteristics corresponding to a particular functional component (or type of functional component) 135, with each of these IR emission reference components 145 being configured to comprise different bias conditions. In this manner, upon identifying a functional component 135 comprising a high current flow, the signal processing module(s) 112 of the IR emission analyser 110 may be arranged to identify a reference component 145 comprising IR emission spectral properties corresponding to those of the identified functional component 135, and that is configured to comprise at least one bias condition corresponding to, or closest to, the bias condition(s) for the identified functional component 135, obtain IR emission information for the identified reference component 145, and determine whether the high current flow of the respective functional component 135 comprises an irregular high current flow based at least partly on a comparison of respective IR emission information for the functional component 135 and the identified reference component 145.

Additionally/alternatively, one or more bias conditions for the (or each) IR emission reference component 145 may be configurable. For example, and as illustrated in FIG. 1, the IR emission reference module 140 may comprise a reference control unit 150, as described in greater detail with reference to FIG. 2 below. In this manner, upon identifying a functional component 135 comprising a high current flow, the signal processing module(s) 112 of the IR emission analyser 110 may be arranged to cause the reference control unit 150 to configure one or more bias conditions of a respective reference component 145 to substantially match or otherwise correspond with the bias conditions of the identified functional component 135, prior to obtaining IR emission information for that reference component 145. For example, and as illustrated in FIGS. 1 and 2, the IC device 105 may comprise an I/O port 160, for example implemented by way of a test/debug port, and via which the signal processing module(s) 112 of the IR emission analyser 110 may be able to control, or otherwise cause, the reference control unit 150 to configure one or more bias conditions for the reference components 145.

Figure 2:
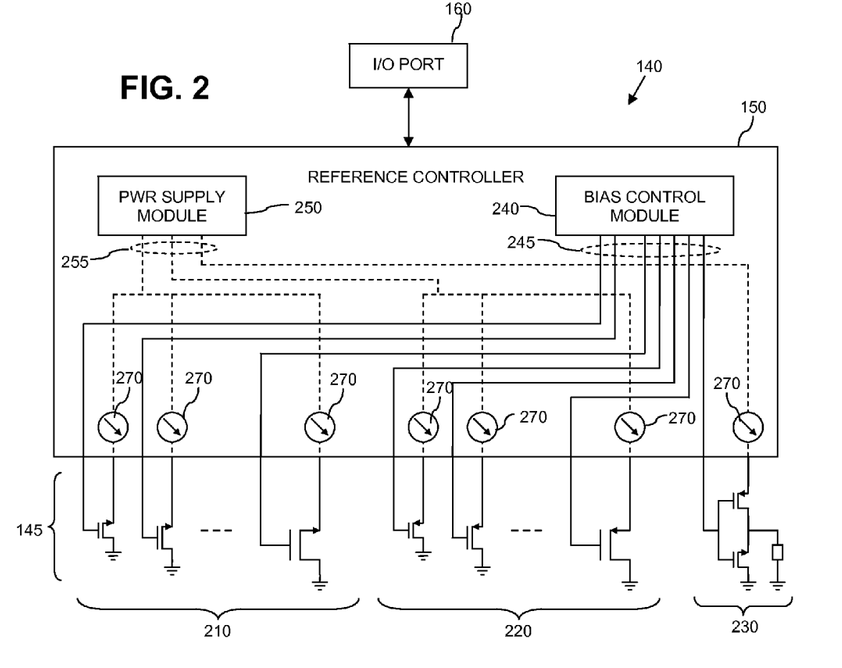
FIG. 2 illustrates a simplified block diagram of an example of an infrared (IR) emission reference module.

FIG. 2 illustrates a simplified block diagram of an example of the IR emission reference module 140 of FIG. 1. In the illustrated example, the IR emission reference module 140 comprises a plurality of IR emission reference components 145. In particular for the illustrated example, the IR emission reference module 140 comprises various different reference components 145 comprising different IR emission spectral characteristics. For example, the IR emission reference module 140 in the illustrated example comprises a plurality of n-channel MOSFET (metal oxide semiconductor field effect transistor) devices 210 of different sizes. In addition, the IR emission reference module 140 in the illustrated example further comprises a plurality of p-channel MOSFET devices 220 of different sizes. In some examples, the IR emission module 140 may additionally/alternatively comprise one or more reference components representative of more complex functional devices 135, for example comprising combinational logic and/or sequential logic. For example, the IR emission module 140 may comprise one or more reference components 145 comprising, say, an inverter (OR gate) reference component 145 as illustrated at 230.

In this manner, the IR emission module 140 may comprise a plurality of IR emission reference components 145 comprising IR emission properties corresponding to a range of different types/sizes/polarities of functional components 135 within the IC device 105. Thus, in some examples, it is contemplated that an IR emission reference component 145 of the same type, size and polarity as a functional component 135 comprising a high current flow may be used as an IR emission reference component therefor.

The IR emission reference module 140 comprises a reference control unit 150 controllable to configure one or more bias conditions of the reference components 145. The reference control unit 150 is arranged to configure, for example in response to commands received via the I/O port 160, one or more bias conditions for the IR emission reference components 145. For example, the reference control module 150 may be arranged to configure bias signal values provided to, in the illustrated example, gate/base junctions of the reference components 145. In the illustrated example, the reference control unit 150 comprises a bias control module 240 arranged to generate individual bias control signals 245 for each of the IR emission reference components 145. In this manner, the bias control module 240 is able to individually configure bias control signal values for the IR emission components 145, for example in response to commands received via the I/O port 160. In some alternative examples, the bias control module 240 may be arranged to generate a single, common bias control signal provided to all of the IR emission components 145, or to generate a reduced set of bias control signals, for example whereby one or more of the bias control signals are provided to two or more of the IR emission components 145, thereby simplifying the implementation and control of the reference control unit 150.

Additionally and/or alternatively, the reference control module 150 may be arranged to configure power supply signal values provided to the reference components 145. In the illustrated example, the reference control unit 150 comprises a power supply control module 250 arranged to generate a power supply signals 255 for the IR emission reference components 145. In this manner, the power supply control module 250 is able to configure power supply signal values for the IR emission components 145, for example in response to commands received via the I/O port 160. In the illustrated example, the power supply control module 250 is arranged to generate a separate power supply signal 255 for each set of the n-channel MOSFET reference components 210, the p-channel MOSFET reference components 210, and the inverter reference component 230. In some alternative examples, the power supply control module 250 may be arranged to generate individual power supply signals for each of the IR emission reference components 145. Alternatively, the power supply control module 250 may be arranged to generate a single, common power supply signal provided to all of the IR emission reference components 145.

In this manner, the reference control unit 150 is able to configure the bias conditions (e.g. bias control signals and/or power supply signals) for the reference components 145, for example to correspond to those of one or more functional components 135 identified as comprising high current flow, thereby configuring the amount of current flowing through the reference components 145.

The reference control unit 150 may additionally/alternatively be arranged to configure a 'type' of current flow; for example the reference control unit 150 may additionally/alternatively be arranged to configure switching current flow representative of a toggling circuit within the IC device 105. Accordingly, in some examples, the reference control unit 150 may be arranged to configure, for example in response to commands received via the I/O port 160, bias conditions for a reference component 145 in order to configure a type of current therefor. For example, the bias control module 240 may be arranged to configure one or more bias control signal profiles provided to a gate/base junction of one or more of the reference components 145. In this manner, the reference control unit 150 is able to configure one or more of the reference components 145 to comprise a particular type of current flow there through, such as a switching current flow. Additionally and/or alternatively, the power supply control module 150 may be arranged to configure one or more power supply signal profiles provided to one or more of the reference components 145. In this manner, a current profile for current flowing through the reference component(s) 145 may further be configurable by the reference control unit 150.

Thus, the method implemented by the signal processing module(s) 112 of the IR emission analyser 110 hereinbefore described, and the implementation of one or more reference modules 140 within the IC device 105 comprising one or more reference components 145, enables irregular high current flow within the IC device 105 to be detected by way of a comparison of IR emission information between functional components 135 and reference components 145, with significantly reduced calibration requirements.

In some examples, the signal processing module(s) 112 of the IR emission analyser 110 may be required not only to determine when current flow within a functional component 135 of the IC device 105 is higher than expected, but also in such cases to determine the current value for such unexpectedly high currents.

Thus, in some examples, the signal processing module(s) 112 of the IR emission analyser 110 may be arranged to perform a comparison of respective IR emission intensities for a functional component 135 identified as comprising a high current flow and a respective reference component 145 under corresponding bias conditions. If the IR emission intensity for the reference component 135 does not substantially match the IR emission intensity for the functional component 135, the signal processing module(s) 112 may further be arranged to modify, for example by way of commands provided to the reference control unit 150, at least one bias condition for the reference component 145 in order to cause the IR emission intensity of the reference component 145 to substantially match the IR emission intensity of the functional component 135. For example, the signal processing module(s) 112 of the IR emission analyser 110 may be arranged to iteratively modify one or more bias conditions for the reference component 145 to cause the IR emission intensity of the at least one reference component to match the IR emission intensity of the at least one functional component. For example, if the IR emission intensity for the reference component 135 does not match the IR emission intensity for the functional component 135, the signal processing module(s) 112 of the IR emission analyser 110 may be arranged to cause the reference control unit 150 to incrementally modify one or more bias conditions for the reference component 145. After each incremental modification, the signal processing module(s) 112 of the IR emission analyser 110 may be arranged to obtain updated IR emission information for the reference component 145 comprising the modified bias conditions, and to compare the updated IR emission information for the reference component 135 to the IR emission information for the functional component 135. In this manner, the signal processing module(s) 112 of the IR emission analyser 110 may be arranged to incrementally modify the bias condition(s) for the reference component until the IR emission intensity therefor substantially matches that of the functional component 135 comprising the high current flow.

Upon achieving an IR emission intensity for the reference component 145 substantially matching that of the functional component 135 comprising a high current flow, the signal processing module(s) 112 of the IR emission analyser 110 may be arranged to obtain a measurement of current flow for the reference component 145 under the modified bias conditions. For example, the power supply control module 250 of the reference control unit 150 may comprise one or more current measuring units 270 arranged to measure a supply current for a respective reference component 145. Accordingly, the signal processing module(s) 112 of the IR emission analyser 110 may be arranged to request, via the I/O port 160, a supply current measurement for one or more of the reference components 145. Accordingly, upon receipt of such a request, the reference control unit may return a measure current value from the respective current measurement unit(s) 270.

Upon receipt of required current measurement, the signal processing module(s) 112 of the IR emission analyser 110 may then determine a current flow value for the respective functional component 135 based at least partly on the measured current flow for the reference component 145. For example, by modifying the bias conditions for the reference component 145 in order to substantially match the IR emission intensity of the reference component 145 to that of the functional component 135, it is reasonable to assume that for comparable components a matching IR emission intensity indicates substantially matching current flow. Thus, the signal process module(s) 112 of the IR emission analyser 110 may be arranged to determine a current flow value for the functional component 135 as being substantially equal to that of the respective reference component 145. In this manner, the method and apparatus hereinbefore described further enable a current flow value for functional components within the IC device to be determined without the need for highly precise calibration of IR emission detection and analysis components, and without requiring invasive probing or the like into the respective functional module 130 in order to obtain a direct current measurement.

Figure 3:
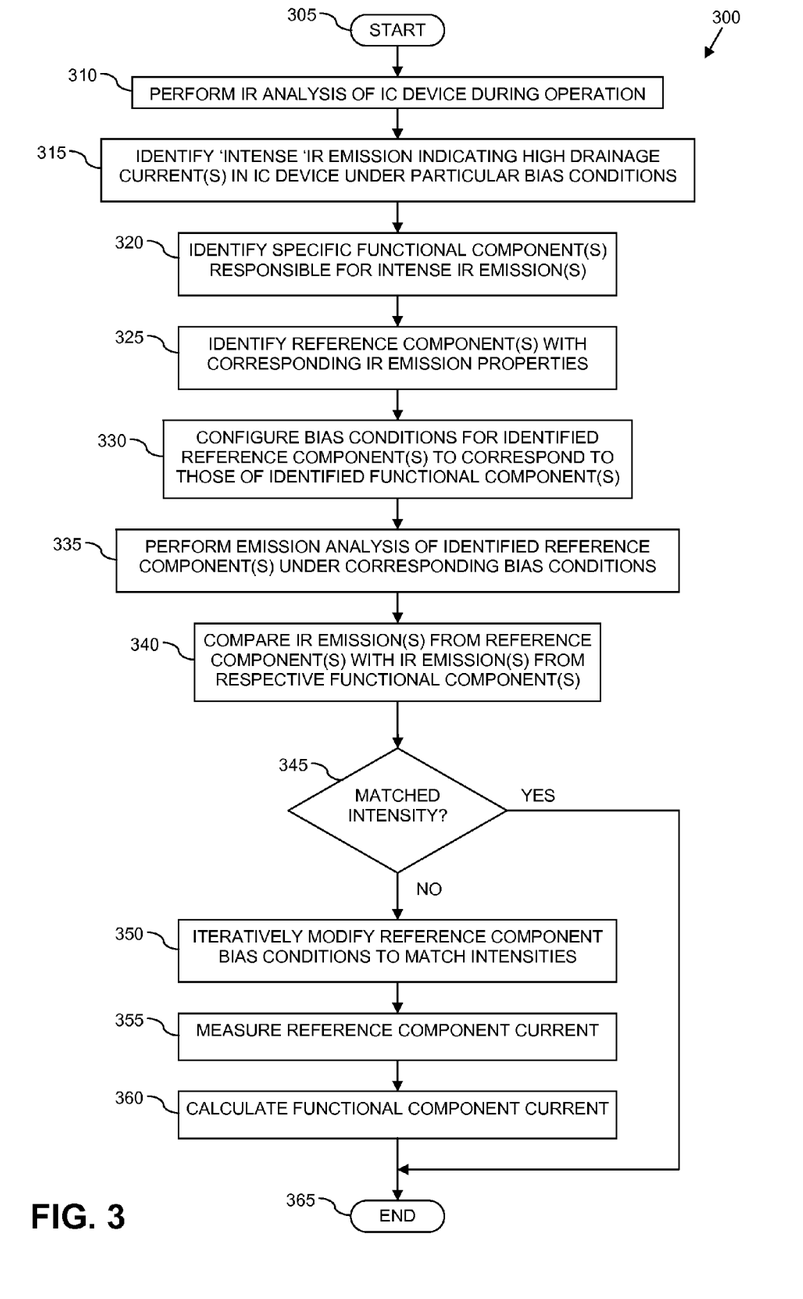
FIG. 3 illustrates a simplified flowchart of an example of a method of detecting irregular high current flow within an IC device.

Referring now to FIG. 3, there is illustrated a simplified flowchart 300 of an example of a method of detecting irregular high current flow within an IC device. The method starts at 305, and moves on to 310 where IR emission information is obtained for an ID device during operation, and in particular for functional components within the IC device. Next, at 315, intense IR emissions indicating high current flows within the IC device are identified. One or more functional components responsible for the intense IR emissions (i.e. comprising high current flow) are then identified at 320. One or more reference components comprising corresponding IR emission properties to those of the identified functional component(s) are then identified, at 325. One or more bias conditions for the identified reference component(s) is/are then configured to correspond to those of the identified functional component(s), at 330. Next, at 335, IR emission information for the identified reference component(s) is obtained, and compared with the IR emission information for the respective identified functional component(s) at 340. If the IR emission intensity for the reference component is substantially matched to that of the respective functional component, it may be determined that the high current flow through the functional component comprises an expected/intended current flow indicative of correct, normal operation of the functional component. Accordingly, in the illustrated example, the method moves on to 365 and ends. Conversely, if the IR emission intensity for the reference component does not substantially match that of the respective functional component, for example is lower than that of the functional component, it may be determined that the high current flow through the functional component comprises an unexpected/irregular current flow indicative of incorrect, problematic operation of the functional component. Accordingly, the method may then move on to 350, where bias conditions for the respective reference component are modified, for example iteratively modified, until the IR emission intensity for the reference component substantially matches that of the functional component. A current measurement for the reference component is then obtained at 355, and a current value for the functional component is then determined, at 360, based on the current measurement for the reference component. The method then ends, at 365.

At least parts of the invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on computer readable storage medium or transmitted to the computer system via a computer readable transmission medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.; and data transmission media including computer networks, point-to-point telecommunication equipment, and carrier wave transmission media, just to name a few.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

As used herein, the expression non-transitory will be understood to refer to the non-ephemeral nature of the storage medium itself rather than to a notion of how long the stored information itself may persist in a stored state. Accordingly, memories that might otherwise be viewed, for example, as being volatile (such as many electronically-erasable programmable read-only memories (EPROM's) or random-access memories (RAM's)) are nevertheless to be viewed here as being 'non-transitory' whereas a signal carrier in transit is to be considered 'transitory' notwithstanding that the signal may remain in transit for a lengthy period of time. Thus, a non-transitory computer program product may comprise at least one of a hard disk, a CD-ROM, an optical storage device, a magnetic storage device, a Read Only Memory, ROM, a Programmable Read Only Memory, PROM, an Erasable Programmable Read Only Memory EPROM, EPROM, an Electrically Erasable Programmable Read Only Memory, EEPROM, and a Flash memory.

In the foregoing specification, the invention has been described with reference to specific examples of embodiments of the invention. It will, however, be evident that various modifications and changes may be made therein without departing from the broader spirit and scope of the invention as set forth in the appended claims.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an', as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an'. The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The invention claimed is:

1. A method of detecting irregular high current flow within an integrated circuit (IC) device, the method comprising:
   obtaining infrared (IR) emission information for the IC device;
   identifying at least one functional component of a plurality of functional components within one or more functional modules of the IC device, the at least one identified functional component comprising a high current flow, based on the obtained IR emission information;
   obtaining IR emission information for a plurality of reference components, wherein each of the plurality of reference components comprising different IR emission spectral properties, the different IR emission spectral properties corresponding to IR emission spectral properties of different ones of the plurality of functional components, wherein the plurality of reference components formed within a reference module of the IC device, and wherein each of the plurality of reference components having individually configured bias conditions that correspond to bias conditions of a different one of the plurality of functional components; and
   determining whether the high current flow of the at least one functional component comprises an irregular high current flow based on a comparison of respective IR emission information for the at least one functional component and a corresponding one of the plurality of reference components.

2. The method of claim 1, wherein the method comprises:
   performing a comparison of the IR emission information for the at least one functional component and IR emission information for the at least one reference component; and
   determining that the high current flow of the at least one functional component comprises an irregular high current flow if an IR emission intensity for the at least one functional component exceeds an IR emission intensity for the at least one reference component.

3. The method of claim 2 wherein the method comprises determining that the high current flow of the at least one functional component comprises an irregular high current flow if an IR emission intensity for the at least one functional component exceeds an IR emission intensity for the at least one reference component by more than a threshold amount.

4. The method of claim 1, wherein the method comprises obtaining IR emission information for the at least one reference component under at least one bias condition corresponding to at least one bias condition of the at least one functional component comprising the high current flow.

5. The method of claim 4, wherein the method comprises configuring the at least one bias condition of the at least one reference component to match the at least one bias condition of the at least one functional component comprising the high current flow, prior to obtaining IR emission information for the at least one reference component.

6. The method of claim 5, wherein the method comprises configuring at least one bias condition of the at least one reference component from a group comprising of at least one of:

at least one power supply signal value provided to the at least one reference component, at least one bias control signal value provided to a gate/base junction of the at least one reference component, at least one power supply signal profile provided to the at least one reference component, and at least one bias control signal profile provided to a gate/base junction of the at least one reference component.

7. The method of claim 4, wherein the method comprises:

performing a comparison of respective IR emission intensities for the at least one functional component and the at least one reference component under corresponding bias conditions; and if the IR emission intensity for the at least one reference component does not match the IR emission intensity for the at least one functional component under corresponding bias conditions, modifying at least one bias condition for the at least one reference component to cause the IR emission intensity of the at least one reference component to match that of the IR emission intensity of the at least one functional component, obtaining a measurement of current flow for the at least one reference component under the modified bias conditions, and determining a current flow value for the at least one functional component based at least partly on the measured current flow for the at least one reference component.

8. The method of claim 7, wherein the method comprises iteratively modifying at least one bias condition for the at least one reference component to cause the IR emission intensity of the at least one reference component to match the IR emission intensity of the at least one functional component, if the IR emission intensity for the at least one reference component does not match the IR emission intensity for the at least one functional component under corresponding bias conditions.

9. The method of claim 1, wherein the method further comprises:

identifying, from a plurality of reference components within the IC device, at least one reference component comprising IR emission spectral properties corresponding to those of the at least one functional component comprising the high current flow;

obtaining IR emission information for at least one identified reference component within the IC device; and determining whether the high current flow of the at least one functional component comprises an irregular high current flow based at least partly on a comparison of respective IR emission information for the at least one functional component and the at least one reference component.

10. An integrated circuit (IC) device comprising at least one functional module arranged to perform at least one operational function of the IC device; the at least one functional module comprising a plurality of functional components; wherein the IC device further comprises at least one infrared (IR) emission reference module comprising a plurality of IR emission reference components, each IR emission reference component of the plurality of IR emission reference components comprising different IR emission spectral properties corresponding to those of the plurality of functional components, and each of the plurality of reference components having individually configured bias conditions that correspond to bias conditions of a different one of the plurality of functional components.

11. The IC device of claim 10, wherein the at least one IR emission reference module further comprises a reference control unit arranged to configure at least one bias condition of the at least one IR emission reference component.

12. The IC device of claim 11, wherein the reference control unit is arranged to configure the at least one bias condition of the at least one IR emission reference component to match at least one corresponding bias condition of the at least one functional component.

13. The IC device of claim 11, wherein the reference control unit is configured to modify the at least one bias condition of the at least one IR emission reference component.

14. The IC device of claim 11, wherein the reference control unit is arranged to configure at least one bias condition of the at least one IR emission reference component from a group comprising of at least one of:

at least one power supply signal value provided to the at least one IR emission reference component;

at least one bias signal value provided to a gate/base junction of the at least one IR emission reference component;

at least one power supply signal profile provided to the at least one IR emission reference component; and at least one bias signal profile provided to a gate/base junction of the at least one IR emission reference component.

15. The IC device of claim 10, wherein the IR emission reference module comprises a plurality of IR emission reference components, the IR emission reference components comprising IR emission spectral properties corresponding to those of a plurality of functional components within the at least one functional module.

* * * * *